United States Patent [19]

Cartwright et al.

[11] Patent Number: 4,992,089
[45] Date of Patent: Feb. 12, 1991

[54] HERBICIDAL COMPOUNDS, COMPOSITIONS AND USE

[75] Inventors: David Cartwright, Reading; David J. Collins, Crowthorne, both of England

[73] Assignee: Imperial Chemical Industries PLC, London, United Kingdom

[21] Appl. No.: 932,101

[22] Filed: Nov. 18, 1986

[30] Foreign Application Priority Data

Nov. 22, 1985 [GB] United Kingdom ............... 8528856

[51] Int. Cl.$^5$ .................... A01N 43/84; A01N 37/18; C07C 243/38; C07D 265/30
[52] U.S. Cl. .......................................... 71/88; 71/94; 71/95; 71/118; 544/164; 546/224; 548/557; 564/150
[58] Field of Search ..................... 544/164; 546/224; 548/557; 564/150; 71/88, 94, 95, 118

[56] References Cited

FOREIGN PATENT DOCUMENTS 2056438 3/1981 United Kingdom .

Primary Examiner—Robert W. Ramsuer
Attorney, Agent, or Firm—Cushman, Darby & Cushman

[57] ABSTRACT

A compound of formula (I)

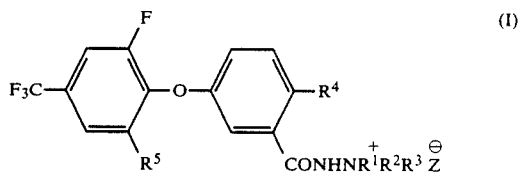

or a zwitterion derivative thereof; wherein $R^1$, $R^2$ and $R^3$ are each independently optionally substituted alkyl or $R^1$ and $R^2$ together with the nitrogen atom to which they are attached form a 5- or 6- membered heterocyclic ring; $R^4$ is hydrogen, nitro, halo, alkyl or $CF_3$; $R^5$ is halo; and $\ominus$ and Z is an anion. The compounds are useful as herbicides.

8 Claims, No Drawings

HERBICIDAL COMPOUNDS, COMPOSITIONS AND USE

This invention relates to diphenyl ether derivatives useful as herbicides and to herbicidal compositions and processes utilising them.

UK published Patent Application No. 2056438A discloses herbicidal diphenyl ether derivatives of the formula (A):

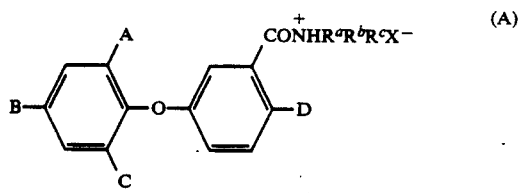

wherein

A is a hydrogen, fluorine, chlorine, bromine or iodine atom or a cyano group, a nitro group, a trifluoromethyl group or an alkyl group of 1 to 4 carbon atoms;

B is a fluorine, chlorine, bromine or iodine atom or a trifluoromethyl group;

C is a hydrogen atom, a fluorine, chlorine, bromine or iodine atom or a trifluoromethyl group;

D is a hydrogen atom or a fluorine, chlorine, bromine or iodine atom, or a nitro group;

$R^a$, $R^b$ and $R^c$ each represent an alkyl radical, or $R^a$ represents an alkyl radical and $R^b$ and $R^c$ together with the nitrogen atom to which they are attached form a five or six membered heterocyclic ring; and X is an anion.

The applicants have found a group of compounds which have improved herbicidal activity and in some instances improved selectivity.

According to the present invention there is provided a compound of formula (I)

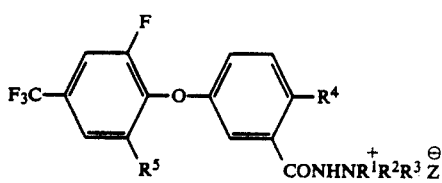

or a zwitterion or imide derivative thereof; wherein $R^1$, $R^2$ and $R^3$ are each independently optionally substituted alkyl or $R^1$ and $R^2$ together with the nitrogen atom to which they are attached form a 5- or 6-membered heterocyclic ring;

$R^4$ is hydrogen, nitro, halo, alkyl or $CF_3$;
$R^5$ is halo; and
and Z is an anion.

When $R^1$, $R^2$ and/or $R^3$ contain an alkyl moiety, the alkyl moiety suitably contain from 1 to 4 carbon atoms.

Suitable optional substituents for $R^1$, $R^2$ and/or $R^3$ include aryl such as phenyl, halo such as chlorine or fluorine, nitrile, haloalkyl such as trifluoromethyl, $CO_2R^6$, $OR^6$ or $S(O)_nR^6$ wherein $R^6$ is hydrogen or a hydrocarbyl group such as $C_{1-6}$ alkyl and n is 0, 1 or 2.

Suitably $R^1$, $R^2$ and $R^3$ are selected from methyl, ethyl or benzyl.

When $R^1$ and $R^2$ form a heterocyclic ring it may be for example a pyrrolidine, piperidine or morpholine ring.

Preferably the heterocyclic ring is a morpholine or piperidine ring.

When $R^4$ is alkyl, it suitably contains from 1 to 4 carbon atoms.

Suitable halo groups for $R^4$ include fluorine, chlorine, bromine and iodine.

Preferably $R^4$ is nitro, chloro or $CF_3$.

Suitable halo groups for $R^5$ include fluorine and chlorine, preferably chlorine.

The anion Z may be any agriculturally acceptable anion. It may be for example a halide anion, preferably a chloride or bromide, or it may be for example a phosphate, nitrate, sulphate, methylsulphate, p-toluene-sulphate or other anion.

The structural formula (I) given above is intended to include tautomeric forms of the structure drawn, as well as physically distinguishable modifications of the compounds which may arise, for example, from different ways in which the molecules are arranged in a crystal lattice, or from the inability of parts of the molecule to rotate freely in relation to other parts, or from geometrical isomerism, or from intra-molecular or inter-molecular hydrogen bonding, or otherwise.

Zwitterionic forms of the compound of formula (I) obviously do not contain anion Z and can be represented by formula (IA)

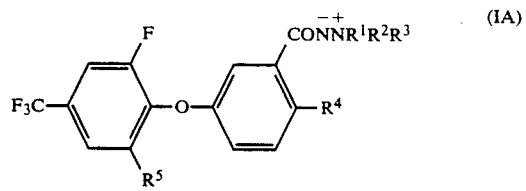

wherein $R^1$, $R^2$, $R^3$, $R^4$ and $R^5$ are as defined in relation to formula (I).

Particular examples of compounds according to the invention and listed in Tables I and II as well as other salts and zwitterions thereof.

TABLE I

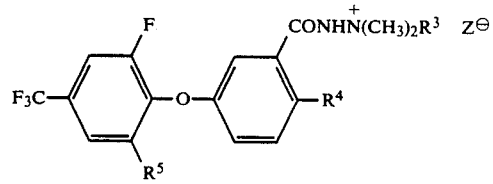

| COMPOUND NO. | $R^3$ | $R^4$ | $R^5$ | $Z^\ominus$ |
|---|---|---|---|---|
| 1 | $CH_2CH_3$ | Cl | Cl | p-toluene sulphate |
| 2 | benzyl | Cl | Cl | bromide |
| 3 | $CH_2CH_3$ | $NO_2$ | Cl | p-toluene sulphate |
| 4 | benzyl | $NO_2$ | Cl | bromide |
| 5 | $CH_3$ | $NO_2$ | Cl | iodide |
| 6 | $CH_3$ | $NO_2$ | Cl | methyl sulphate |
| 7 | $CH_3$ | $NO_2$ | F | methyl sulphate |
| 8 | $CH_3$ | Cl | Cl | iodide |
| 9 | $CH_3$ | Cl | F | methyl sulphate |
| 14 | $CH_3$ | Cl | Cl | methyl sulphate |
| 15 | $CH_2CH_3$ | $NO_2$ | F | p-toluene sulphate |

TABLE II

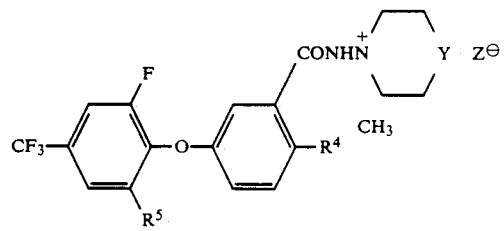

| COMPOUND NO. | R⁴ | R⁵ | Y | Z |
|---|---|---|---|---|
| 10 | $NO_2$ | Cl | —O— | p-toluene sulphate |
| 11 | Cl | Cl | —O— | p-toluene sulphate |
| 12 | Cl | Cl | $CH_2$ | p-toluene sulphate |
| 13 | $NO_2$ | Cl | $CH_2$ | p-toluene sulphate |

The compounds of formula (I) are suitably prepared by quaternisation of a compound of formula (II)

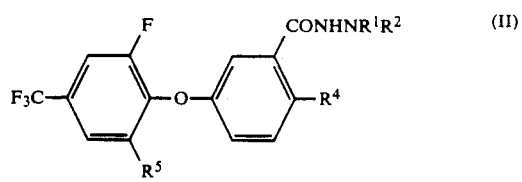

wherein $R^1$, $R^2$, $R^4$ and $R^5$ are as defined in relation to formula (I) with a compound of formula (III)

$$R^3\text{—}Z \qquad (III)$$

wherein $R^3$ and Z are as defined in relation to formula (I) and thereafter if desired carrying out one or more of the following steps
(i) converting the anion Z to a different anion;
(ii) forming a zwitterion or imide of the compound of formula (IA).

The reaction is suitably carried out under conventional conditions, depending upon the nature of the compound of formula III.

Suitably, when Z is, for example, halide such as bromide or iodide, the reaction is carried out in an organic solvent. Examples of suitable solvents include the lower alkanols, for example methanol, ethanol and propanol, and polar solvents such as dimethylformamide and nitrobenzene. The quaternisation reaction may be accelerated by heating, for example to a temperature of from 50° to 120° C.

Alternatively when Z is for example p-toluene sulphate, the reaction may be carried out by fusing the compound of formula (II) with the compound of formula (III) at elevated temperatures, for example from 100° to 200° C. depending upon the particular compound of formula (III) employed.

Exchange of one anion Z for another can be carried out using conventional methods. For example by passing a solution of the salt of formula (I) through a bed of an ion exchange resin loaded with the appropriate anion.

Compounds of formula (I) may be converted to the corresponding internal zwitterion or imide of formula (IA) by treatment with alkali in aqueous medium.

Compounds of formula (II) are novel and as such form part of the invention. They may have herbicidal activity in their own right.

Compounds of formula (II) can be prepared by reaction of a compound of formula (IV)

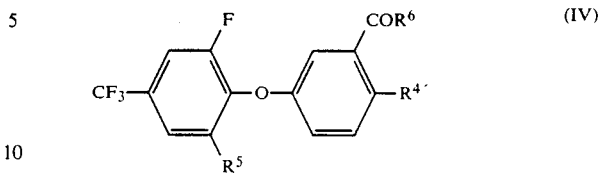

wherein $R^4$ and $R^5$ are as defined in relation to formula (I); and $R^6$ is an acid activating group such as halide, in particular chloride, or an alkoxy group such as $C_{1-6}$ alkoxy; with a hydrazine derivative of formula (V)

$$R^1R^2N\text{—}NH_2 \qquad (V)$$

wherein $R^1$ and $R^2$ are as defined in relation to formula (I).

The reaction is suitably carried out in an inert organic solvent such as toluene at moderate or depressed temperature for example of from 0–30° C.

Optionally the reaction can be carried out in the presence of an acid acceptor. Examples of acid acceptors include tertiary amines, for example triethylamine, and alkali metal carbonates, for example potassium carbonate.

Compounds of formula (IV) can be prepared by activation of a compound of formula (VI)

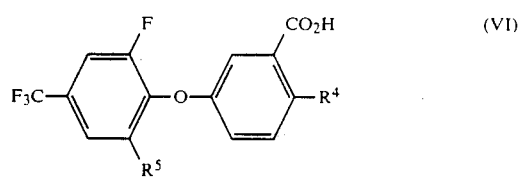

wherein $R^4$ and $R^5$ are as defined in relation to formula (I). The activation reaction can be carried out by conventional means for example using a halogenating agent or an esterifying agent.

Preferably the compound of formula (VI) is reacted with a chlorinating agent for example thionyl chloride, phosphorus oxychloride or phosphorus pentachloride. The reaction may be accelerated by heating for example to a temperature of from 50° to 150° C.

Compounds of formula (VI) are known compounds or can be made from known compounds by known methods (see for example European Published Patent Application No. 0034402A).

One preparation of compounds of formula (I) can be summarised as shown in Scheme A.

Scheme A

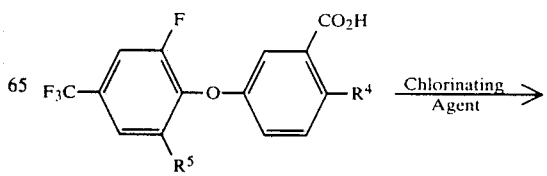

-continued
Scheme A

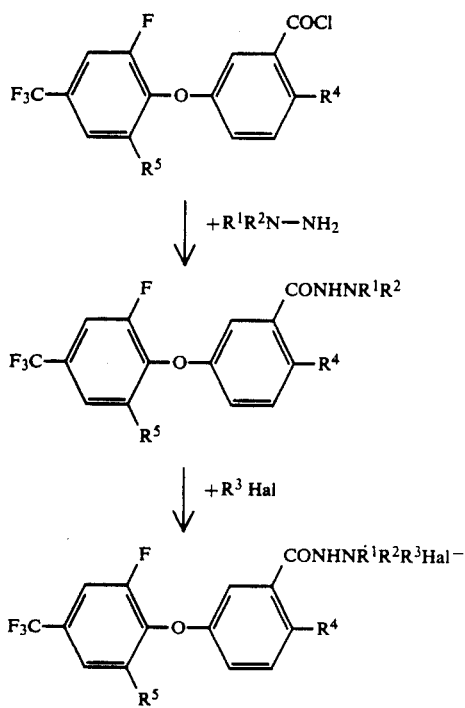

The compounds of the invention are broad-spectrum herbicides capable of controlling the growth of a wide variety of plants although certain of the compounds show a useful selectivity in crops such as soya. The selectivity of any particular compound can be readily established by the skilled man by routine techniques. They may be applied to the soil before the emergence of plants (pre-emergence application) or they may be applied to the above ground parts of growing plants (post-emergence application). In another aspect, therefore, the invention provides a process of inhibiting the growth of unwanted plants, by applying to the plants, or to the locus thereof, a compound of the formula (I) as hereinbefore defined.

The rate of application required to inhibit the growth of unwanted plants will depend on, for example, the particular compound of formula (I) chosen for use, and the particular species of plant it is desired to control. However, as a general guide, an amount of from 0.01 to 5.0 kilograms per hectare, and preferably 0.05 to 2 kilograms per hectare is usually suitable.

The compounds of the invention are preferably applied in the form of a composition, in which the active ingredient is mixed with a carrier comprising a solid or liquid diluent. In another aspect, therefore, the invention provides a herbicidal composition, comprising as an active ingredient a compound of the formula (I) as hereinbefore defined, in admixture with a solid or liquid diluent. Preferably the composition also comprises a surface active agent.

The solid compositions of the invention may be for example, in the form of dusting powders, or may take the form of granules. Suitable solid diluents include, for example, kaolin, bentonite, kieselguhr, dolomite, calcium carbonate, talc, powdered magnesia, and Fuller's earth. Solid compositions also include soluble powders and granules which may comprise a compound of the invention in admixture with a water-soluble carrier.

Solid comPositions may also be in the form of dispersible powders or grains comprising in addition to the active ingredient, a wetting agent to facilitate the dispersion of the powder or grains in liquids. Such powders or grains may include fillers, suspending agents and the like.

Liquid compositions include solutions, dispersions and emulsions containing the active ingredient preferably in the presence of one or more surface active agents. Water or organic liquids may be used to prepare solutions, dispersions, or emulsions of the active ingredient. The liquid compositions of the invention may also contain one or more corrosion inhibitors for example lauryl isoquinolinium bromide.

Surface active agents may be of the cationic, anionic or non-ionic type. Suitable agents of the cationic type include for example quaternary ammonium compounds, for example cetyltrimethyl ammonium bromide. Suitable agents of the anionic type include for example soaps, salts of aliphatic mono-esters of sulphuric acid, for example sodium lauryl sulphate; and salts of sulphonated aromatic compounds, for example dodecylbenzenesulphonate, sodium, calcium and ammonium ligno-sulphonate, butylnaphthalene sulphonate, and a mixture of the sodium salts of diisopropyl- and triisopropyl-naphthalenesulphonic acid. Suitable agents of the non-ionic type include, for example, the condensation products of ethylene oxide with fatty alcohols such as oleyl alcohol and cetyl alcohol, or with alkyl phenols such as octyl-phenol, nonylphenol, and octylcresol. Other non-ionic agents are the partial esters derived from long chain fatty acids and hexitol anhydrides, for example sorbitol monolaurate; the condensation products of the said partial esters with ethylene oxide and the lecithins.

The compositions which are to be used in the form of aqueous solutions, dispersions or emulsions are generally supplied in the form of a concentrate containing a high proportion of the active ingredient, the concentrate being diluted with water before use. These concentrates are usually required to withstand storage for prolonged periods and after such storage to be capable of dilution with water in order to form aqueous preparations which remain homogeneous for a sufficient time to enable them to be applied by conventional spray equipment.

The compositions of the invention may contain, in addition to carriers and surface active agents, various other constituents to increase their usefulness. They may contain, for example, buffering salts to maintain the pH of the composition within a desired range; antifreeze agents, for example urea or propylene glycol; adjuvants, for example oils and humectants; and sequestrants, for example citric acid and ethylenediaminetetracetic acid, which help to prevent the formation of insoluble precipitates when the compositions are diluted with hard water. Aqueous dispersions may contain anti-settling agents and anti-caking agents. The compositions may in general contain a dye or pigment to impart a characteristic colour. Agents for increasing viscosity may be added to reduce the formation of fine droplets during spraying, and thereby reduce spray drift. Other additives useful for particular purposes will be known to those skilled in the formulation art.

In general, concentrates may conveniently contain from 10 to 85% and preferably from 25 to 60% by weight of active ingredient. Dilute preparations ready for use may contain varying amounts of the active ingredient, depending upon the purpose for which they are to be used; however, dilute preparations suitable for many uses contain between 0.01% and 10% and preferably between 0.1% and 1% by weight of the active ingredient. The compounds of the invention can be used in association with another herbicide, for example in the form of a mixture or in a composition of the invention. The other herbicide will generally be a herbicide having a complementary action, depending upon the particular utility and circumstances of administration.

Examples of useful complementary herbicides are: For example it may be desirable in certain circumstances to use the compound of formula (II) or (IIA) in admixture with a contact herbicide.

Examples of useful complementary herbicides include:

A. benzo-2,1,3-thiadiazin-4-one-2,2-dioxides such as 3-isopropylbenzo-2,1,3-thiadiazin-4-one-2,2-dioxide (bentazon);

B. hormone herbicides, particularly the phenoxy alkanoic acids such as 4-chloro-2-methylphenoxy acetic acid (MCPA), 2-(2,4-dichlorophenoxy)propionic acid (dichlorprop), 2,4,5-trichlorophenoxyacetic acid (2,4,5-T), 4-(4-chloro-2-methylphenoxy)butyric acid (MCPB), 2,4-dichlorophenoxyacetic acid (2,4-D), 4-(2,4-dichlorophenoxy)butyric acid (2,4-DB), 2-(4-chloro-2-methylphenoxy)propionic acid (mecoprop), and their derivatives (eg. salts, esters and amides);

C. 3-[4-(4-halophenoxy)phenyl]-1,1-dialkylureas such as 3-[4-(4-chlorophenoxy)phenyl]-1,1-dimethylurea.

D. Dinitrophenols and their derivatives (eg. acetates) such as 2-methyl-4,6-dinitrophenol (DNOC), 2-t-butyl-4,6-dinitrophenol (dinoterb), 2-secbutyl-4,6-dinitrophenol (dinoseb) and its ester, dinoseb acetate;

E. dinitroaniline herbicides such as N',N'-diethyl-2,6-dinitro-4-trifluoromethyl-m-phenylenediamine (dinitramine), 2,6-dinitro-N,N-dipropyl-4-trifluoromethylaniline (trifluralin) and 4-methylsulphonyl-2,6-dinitro-N,N-dipropylaniline (nitralin);

F. phenylurea herbicides such as N'-(3,4-dichlorophenyl)-N,N-dimethylurea (diuron) and N,N-dimethyl-N'-[3-(trifluoromethyl)phenyl]urea (flumeturon);

G. phenylcarbamoyloxyphenylcarbamates such as 3-[methoxy carbonylamino]phenyl (3-methylphenyl)-carbamate (phenmedipham) and 3-[ethoxycarbonylamino]-phenyl phenylcarbamate (desmedipham);

H. 2-phenylpyridazin-3-ones such as 5-amino-4-chloro-2-phenylpyridazin-3-one (pyrazon);

I. uracil herbicides such as 3-cyclohexyl-5,6-trimethyleneuracil (lenacil), 5-bromo-3-sec-butyl-6-methyl-uracil (bromacil) and 3-t-butyl-5-chloro-6-methyl-uracil (terbacil);

J. triazine herbicides such as 2-chloro-4-ethylamino-6-(i-propylamino)-1,3,5-triazine (atrazine), 2-chloro-4,6-di(ethylamino)-1,3,5-triazine (simazine) and 2-azido-4-(i-propylamino)-6-methylthio-1,3,5-triazine (aziprotryne);

K. 1-alkoxy-1-alkyl-3-phenylurea herbicides such as 3-(3,4-dichlorophenyl)-1-methoxy-1-methylurea (linuron), 3-(4-chlorophenyl)-1-methoxy-1-methylurea (monolinuron), 3-(4-bromo-4-chlorophenyl)-1-methoxy-1-methylurea (chlorbromuron).

L. thiolcarbamate herbicides such as S-propyl dipropyl-thiocarbamate (vernolate);

M. 1,2,4-triazin-5-one herbicides such as 4-amino-4,5-dihydro-3-methyl-6-phenyl-1,2,4-triazine-5-one (metamitron) and %b 4-amino-6-t-butyl-4,5-dihydro-3-methylthio-1,3,4-triazin-5-one (metribuzin);

N. benzoic acid herbicides such as 2,3,6-trichlorobenzoic acid (2,3,6-TBA), 3,6-dichloro-2-methoxybenzoic acid (dicamba) and 3-amino-2,5-dichlorobenzoic acid (chloramben);

O. anilide herbicides such as N-butoxymethyl-chloro-2',6'-diethylacetanilide (butachlor), the corresponding N-methoxy compound (alachlor), the corresponding N-i-propyl compound (propachlor), 3',4'-dichloropropionanilide (propanil) and 2-chloro-N-[pyrazol-1-ylmethyl]acet-2'-6'-xylidide (metazachlor);

P. dihalobenzonitrile herbicides such as 2,6-dichlorobenzonitrile (dichlobenil), 3,5-dibromo-4-hydroxybenzonitrile (bromoxynil) and 3,5-diiodo-4-hydroxybenzonitrile (ioxynil);

Q. haloalkanoic herbicides such as 2,2-dichloropropionic acid (dalapon), trichloroacetic acid (TCA) and salts thereof;

R. diphenylether herbicides such as 4-nitrophenyl 2-nitro-4-trifluoromethylphenyl ether (fluorodifen), methyl 5-(2,4-dichlorophenoxy)-2-nitrobenzoate (bifenox), 2-nitro-5-(2-chloro-4-trifluoromethylphenoxy)benzoic acid (acifluorfen) and salts and esters thereof, 2-chloro-4-trifluoromethylphenyl 3-ethoxy-4-nitrophenyl ether (oxyfluorfen) and 5-(2-chloro-4-(trifluoromethyl)phenoxy)-N-(methylsulfonyl)-2-nitrobenzamide (fomesafen), 5-(2-chloro-6-fluoro-4-(trifluoromethyl)phenoxy)-N-(ethylsulhonyl)-2-nitrobenzamide (halosafen); and S. phenoxyphenoxypropionate herbicides such as 2-(4-(4'-trifluoromethylphenoxy)-phenoxy)-propionic acid methylester (trifop-methyl), 2-(4-((5-trifluoromethyl)-2-(pyridinyl)oxy)phenoxypropanoic acid (fluazifop) and esters thereof, 2-(4-((3-chloro-5-trifluoromethyl)-2-pyridinyl)oxy)phenoxy)propanoic acid (haloxyfop) and esters thereof, 2-(4-((6-chloro-2-quinoxalinyl)oxy)phenoxypropanoic acid (xylofop) and esters thereof; and T. cyclohexanedione herbicides such as 2,2-dimethyl-4,6-dioxo-5-(1-((2-propenyloxy)amino)-butylidine) cyclohexane carboxylic acid (alloxydim) and salts thereof, 2-(1-ethoxyimino)butyl-5-(2-(ethylthio)-propyl)-3-hydroxy-2-cyclohexen-1-one (sethoxydim), 2-(1-(3-chloroallyloxyimino)butyl)-5-(2-ethylthiopropyl)-3-hydroxy cyclohex-2-enone (cloproxydim), 2-(1-ethoxyimino)butyl)-3-hydroxy-5-thian-3-yl cyclohex-2-enone (cycloxydim); and U. sulfonyl urea herbicides such as 2-chloro-N-(4-methoxy-6-methyl-1,3,5-triazin-2-yl)-aminocarbonyl) benzenesulphonamide (chlorosulfuron), methyl 2-((((4,6-dimethyl-2-pyrimidinyl)amino)carbonyl)amino)-sulphonylbenzoic acid (sulfometuron), 2-(((3-(4-methoxy-6-methyl-1,3,5-triazin-2-yl)carbonyl)amino)-sulphonyl)benzoic acid (metsulfuron) and esters thereof;

V. imidazolidinone herbicides such as 2-(4,5-dihydro-4-isopropyl-4-methyl-5-oxoimidazol-2-yl)quinoline-3-carboxylic acid (imazaquin), methyl 6-(4-isopropyl-4-methyl-5-oxo-2-imidazolin-2-yl)-m-toluate and p-toluate isomer (AC 222293)

W. arylanilide herbicides such as 1-methylethyl-N-benzoyl-N-(3-chloro-4-fluorophenyl)-L-alanine (flamprop-isopropyl), ethyl N-benzoyl-N-(3,4-dichlorophenyl)-DL-alaninate (benzoylprop-ethyl), N-(2,4-difluorophenyl)-2-(3-(trifluoromethyl)-phenoxy)-3-pyridinecarboxamide (diflufenican); and X. amino acid herbicides such as N-(phosphonomethyl)glycine (glyphosate) and DL-homoalanin-4-yl(methyl)phosphinic acid (phosphinothricin) and their salts and esters; and
Y. organoarsenical herbicides such as monosodium methanearsonate (MSMA); and
Z. miscellaneous herbicides including N,N-dimethyldiphenylacetamide (diphenamid), N-(1-naphthyl)phthalamic acid (naptalam) and 3-amino-1,2,4-triazole, 2-ethoxy-2,3-dihydro-3,3-dimethylbenzofuran methanesulfonate (ethofumesate), 1,4-epoxy-p-meth-2-yl 2-methylbenzyl ether (cinmethylin), 2-(2-chlorophenyl)methyl-4,4-dimethyl-3-isoxazolidinone (dimethazone);

Examples of useful contact herbicides include:

bipyridylium herbicides such as those in which the active entity is the 1,1'-dimethyl-4,4'-dipyridylium ion (paraquat) and those in which the active entity is the 1,1')ethylene-2,2'-dipyridylium ion (diquat);

The complementary herbicide is suitably present in the mixture or composition in an amount such that it is applied at its conventional rate.

The following Examples illustrate the invention.

EXAMPLE 1

This Example illustrates the preparation of compound No. 1 in Table I.

(a) Preparation of 2-chloro-5-(2-chloro-6-fluoro-4-trifluoromethylphenoxy)benzoyl chloride 2-Chloro-5-(2-fluoro-4-trifluoromethyl-6-chlorophenoxy)benzoic acid (3.69g) was dissolved in thionyl chloride (20 cm$^3$) and refluxed for 2 hours. Following concentration, the solution was azeotroped with toluene and the required acid chloride derivative obtained as an oil.

(b) Preparation of N-[2-chloro-5-(2-chloro-6-fluoro-4-trifluoromethylphenoxy)benzoyl]-N',N'-dimethylhydrazide The product from (a) was dissolved in dry toluene (20 cm$^3$) and cooled in an ice bath. A solution of dimethyl hydrazine (1.2g) in dry toluene (5 cm$^3$) was added dropwise and the mixture was stirred at room temperature for 6 hours after which it was left to stand overnight. The solution was then partitioned between ether and water and the organic layer separated, washed with water/brine and dried. Concentration of this solution gave a yellow oil. Following trituration of the oil with cold petrol (30/40), the required hydrazide derivative was obtained as a white solid (yield 2.19g mp. 115–117° C.).

(c) Compound No. 1 in Table I

The product from step (b) (1g) was fused with an excess of ethyl-p-toluene sulphonate (1.5g) at 140° C. for 6 hours. Following extraction into ethyl acetate, the ethyl acetate fraction was concentrated to a sticky oil which was gently heated and placed under a high vacuum for several hours to remove the solvent.

An oily gum (0.46g) was obtained which was confirmed by nmr and molecular analysis to be compound No. 1 of Table I.

EXAMPLE 2

This Example illustrates the preparation of Compound No. 2 of Table I.

N-[2-chloro-5-(2-chloro-6-fluoro-4-trifluoromethyl phenoxy)benzoyl]-N'N'-dimethylhydrazide (1g) produced as described in Example 1(b) was dissolved in ethanol (15 cm$^3$) and an excess of benzyl bromide (1.5 cm$^3$) added. The resultant solution was stirred at room temperature for 4 hours and then left to stand for two days. After concentration, an oily gum was obtained which was triturated first with ether and then with cyclohexane to yield compound No. 2 of Table 2 as a yellow/white solid (yield 0.67g; m.p. 68–71° C.).

EXAMPLE 3

This Example illustrates the preparation of Compound No. 3 in Table I.

(a) preparation of 2-nitro-5-(2-chloro-6-fluoro-4-trifluoromethyl-phenoxy)benzoyl chloride 2-Nitro-5-(2-chloro-6-fluoro-4-trifluoromethyl phenoxy)benzoic acid (1.9g) was dissolved in thionyl chloride (10 cm$^3$) and refluxed for 2 hours. The product was concentrated and azeotroped to yield the required acid chloride derivative in the form of an oil.

(b) Preparation of N-[2-nitro-5-(2-chloro-6-fluoro-4-trifluoromethylphenoxy)benzoyl]-N', N'-dimethylhydrazide The product from Example 2(a) was dissolved in dry toluene (15 cm$^3$) and cooled in an ice bath. 0.6g of dimethyl hydrazine in toluene (5 cm$^3$) was then added dropwise with stirring and stirring was continued for 1½hours. The resultant solution was poured into excess water and extracted into ether. After washing, drying and concentration of the ether extract, a semi-solid product was obtained. Trituration of this product with petrol (30/40) gave a yellow-white solid (1.66g) which was confirmed by nmr analysis to be the desired hydrazide.

(c) Compound No. 3 in Table I

The product from Example 3(b) (1g) was fused with ethyl-p-toluene sulphate at 140° C. for 6 hours. Following trituration with cyclohexane, a solid gum was obtained which was dried under reduced pressure at 80° C. for 8 hours. Elemental analysis confirmed that this was the Compound No. 3 in Table I.

EXAMPLE 4

This Example illustrates the preparation of Compound No. 4 in Table I.

N-[2-nitro-5-(2-chloro-6-fluoro-4-trifluoromethyl phenoxy)benzoyl]-N',N'-dimethylhydrazide (1g) produced as described in Example 3(b) was dissolved in ethanol and an excess of benzyl bromide (1.5 cm$^3$) was added dropwise. The mixture was stirred for 2 hours and then left to stand overnight, after which the solvent was removed to give an orange-brown oil. Trituration of this oil with ether and then petrol (40/60) produced Compound No. 4 in Table I as a yellowy solid (yield 0.81g, mp. 93–96° C.).

EXAMPLE 5

This Example illustrates the preparation of Compound No. 5 in Table I.

N-[2-nitro-5-(2-chloro-6-fluoro-4-trifluoromethyl phenoxy)benzoyl]-N',N'-dimethylhydrazide (0.69g), prepared by methods similar to those described in Example 3(b) was dissolved in methanol (4 cm$^3$) and an excess of methyl iodide (2 cm$^3$) was added dropwise. The mixture was stirred under reflux for 3 hours and then concentrated to a yellow sticky solid. Trituration first with ether and then with hexane yielded Compound No. 5 in Table I as a yellow solid (0.55g, mp. 150–153° C.).

EXAMPLE 6

Compound No. 6 in Table I was prepared in an analogous manner to that described in Example 5 above but using dimethyl sulphate instead of methyl iodide. The trituration with hexane was not carried out.

EXAMPLE 7

This Example illustrates the preparation of Compound No. 7 in Table I.

(a) Preparation of 2-nitro-5-(2,6-difluoro-4-trifluoromethylphenoxy)benzoyl chloride 2-Nitro-3-(2,6-difluoro-4-trifluoromethylphenoxy)-benzoic acid (1.3g) was refluxed with thionyl chloride (10 cm$^3$) for one hour.

The resultant solution was concentrated, azeotroped with toluene to give the desired acid chloride in the form of an oil.

(b) Preparation of N-[2-nitro-5-(2,6-difluoro-4-trifluoromethylphenoxy)-benzoyl]-N',N'-dimethylhydrazide The product from Example 7(a) was dissolved in toluene (10 cm$^3$) and cooled in an ice bath. A solution of N,N-dimethylhydrazine (0.44g) in toluene (~2.3 cm$^3$) was added dropwise. The resultant solution was stirred for 4 hours at room temperature and allowed to stand overnight. It was then concentrated to an oil to which water was added. The mixture was extracted into ether and the ether extract washed with water/brine, dried and concentrated to give an oil. Trituration with petrol (40/60) gave the title compound as an off-white solid (0.83g), the structure of which was confirmed by nmr analysis.

(c) Compound No. 7 in Table I

A sample of N-[2-nitro-3-(2,6-difluoro-4-trifluoromethylphenoxy)benzoyl]-N',N'-dimethylhydrazide (0.47g), prepared as described in Example 7(b) was dissolved in toluene (10 cm$^3$) and a solution of dimethyl sulphate (0.15g) in toluene (5 cm$^3$) was added dropwise. The solution was stirred under reflux for 4 hours after which it was left to stand overnight. Concentration of the solution on a rotary evaporator produced an oily residue which was triturated with ether to give a brown solid. The resultant solid was dried at 90° C. under reduced pressure to yield Compound No. 8 in Table I (0.39g, mp. 139–143° C.).

EXAMPLE 8

This Example illustrates the preparation of Compound No. 8 in Table I.

N-[2-chloro-5-(2-chloro-6-fluoro-4-trifluoromethyl phenoxy)benzoyl]-N',N'-dimethyl hydrazide (1.0g) prepared as described in Example 1(b) was dissolved in methanol (5 cm$^3$) and an excess of methyl iodide (3 cm$^3$) was added. The solution was refluxed for 5 hours and then left overnight at room temperature. Following concentration to remove solvent, an orange sticky solid was obtained and was triturated with ether to give Compound No. 8 in Table I as an off-white solid (1.20g, mp. 151–4° C.).

EXAMPLE 9

This Example illustrates the preparation of Compound No. 9 in Table I.

(a) Preparation of N-[2-chloro-5-(2,6-difluoro-4-trifluoromethylphenoxy)-benozyl]-N',N'-dimethyl hydrazide The title compound was prepared from 2-chloro-5-(2,6-difluoro-4-trifluoromethylphenoxy)benzoic acid by way of the corresponding acid chloride by methods analogous to those described in Example 7(a) and 7(b). The product was isolated as a white solid (0.83g). The structure of which was confirmed by nmr and elemental analysis.

(b) Preparation of Compound No. 9 in Table I

The product from Example 9(a) was dissolved in dry toluene (7 cm$^3$) and a solution of dimethylsulphate (0.2g) in dry toluene (3 cm$^3$) added. The solution was stirred under reflux for 4½ hours and left to stand overnight at room temperature. After concentration to an oily solid, ether and petrol were added and a solid filtered off which turned to a gum on standing. The gum was dried in an oven at about 70° under vacuum and Compound No. 9 in Table I was obtained as a brown powder (0.50g, mp. 146–149° C.).

EXAMPLE 10

This Example illustrates the preparation of Compound No. 10 in Table II.

(a) Preparation of N'[2-nitro-5-(2-chloro-6-fluoro-4-trifluoro-methyl-6-chlorophenoxy)benzoyl]amino morpholine The acid chloride of 2-nitro-5-(2-chloro-6-fluoro-4-trifluoromethyl-phenoxy)benzoic acid (2.28g) was prepared as described in Example 3(a) in the form of an oil. This oil was dissolved in toluene (20 cm$^3$) and cooled to a temperature of less than 10° C. in an ice/salt bath. Triethylamine (2 cm$^3$) was added and subsequently a solution of N-amino-morpholine (1.23g) was added dropwise, the temperature being maintained below 10° C. throughout the additions. The reactants were then allowed to return to room temperature, stirred and left to stand overnight. The solution was poured into excess water and then extracted into ether. After washing and drying, the ether extract was concentrated to give a yellow solid residue. Cold ether was added to this residue whereupon the title compound in the form of a white solid was obtained (yield 1.88g, mp. 92–95° C.).

(b) Compound No. 10 in Table II

The product (1g) from Example 11(a) was fused with methyl-p-toluene sulphate (07.2g) at 140° C. for 8 hours. After cooling and trituration with ether and pentane alternately, a white solid was obtained which was filtered and air-dried. This compound was found by nmr and elemental analysis to be Compound No. 10 in Table II (yield 0.83g, sublimes).

EXAMPLE 11

This Example illustrates the preparation of Compound No. 11 in Table II.

The acid chloride of 2-chloro-5-(2-chloro-6-fluoro-4-trifluoromethylphenoxy)benzoic acid (1g) was prepared as described in Example 1(a) and then mixed dropwise with N-amino-morpholine (0.28g) and an excess of methyl-p-toluene sulphonate (1.5g) at room temperature. The reaction mixture was stirred and then fused at about 160° C. for 2 hours and then heated for a further 2 hours at 185° C. The product was then extracted into ethyl acetate, filtered and concentrated to give Compound No. 11 in Table II as an orange oil (0.98g). The structure of the oil was confirmed by nmr and elemental analysis.

EXAMPLE 12

This Example illustrates the preparation of Compound No. 12 in Table II.

(a) Preparation of
N'[2-chloro-5-(2-chloro-6-fluoro-4-trifluoromethylphenoxy)benzoylamino]-piperidine The acid chloride of 2-chloro-5-(2-chloro-6-fluoro-4-trifluoromethyl-phenoxy)benzoic acid (1g) was prepared as described in Example 1(a). The resultant oil was dissolved in dry toluene, cooled in an ice bath and triethylamine (0.5 cm$^3$) added. The resultant solution was stirred and maintained at a temperature of about 5° C. whilst N-aminopiperidine (0.5g) in dry toluene (5 cm$^3$) was added dropwise. After stirring for 1 hour at a temperature of 10° C. or less, the reaction mixture was poured into excess water and extracted into ether. The ether extract was washed and concentrated to give an oil. Trituration of the oil with pentane gave the title compound as a white solid (0.99g, mp. 106–109° C.).

(b) Compound No. 12 in Table II

The product from Example 12(a) (0.69g) was fused with p-methyl sulphonate (0.57g) at 140° C. with stirring for 6 hours. It was then left to stand overnight at room temperature and a glass product obtained. After trituration with ether and then petrol, a sticky white solid was obtained. Upon addition of a small volume of ethyl acetate, Compound No. 12 in Table II precipitated as a white solid (0.58g, m.p 155–158 ° C.).

EXAMPLE 13

This Example illustrates the preparation of Compound No. 13 in Table II.

(a) Preparation of
N-[2-nitro-5-(2-chloro-6-fluoro-4-trifluoromethylphenoxy)benzoylamino]piperidine The acid chloride of 2-nitro-5-(2-chloro-6-fluoro-4-trifluoro-methyl-phenoxy)benzoic acid (2.28g) prepared as described in Example 3(a), was dissolved in dry toluene (20 cm$^3$) and cooled in an ice/salt bath. Triethylamine (2 cm$^3$) was added followed by the dropwise addition of N-aminopiperidine (1.2g) in dry toluene, the temperature being maintained at 10° C. or less during the additions. After stirring, the reaction mixture was left to stand at room temperature overnight. It was then poured into an excess of water and extracted into ethylacetate. The ethyl acetate extract was washed, dried and concentrated to give an oil. This oil was separated by h.p.l.c using an ether/hexane/acetic acid eluent.

The title compound was isolated as a white solid (yield 1.5g, mp. 65–68° C.).

(b) Compound No. 13 in Table II

The product (0.9g) from Example 13(a) was fused with methyl-p-toluene sulphate (0.5g) at 140° C. for 4 hours and then left to stand overnight. It was then dissolved in ethyl acetate and the solution concentrated until a solid formed which was filtered off and washed with pentane and ether. At this point the product was a sticky oil which was again dissolved in ethyl acetate, charcoaled and dried over magnesium sulphate to give the Compound No. 13 in Table II as an off-white solid (0.72g; sublimes).

EXAMPLE 14

This Example illustrates the preparation of compound No. 14 in Table I.

N-[2-chloro-5-(2-chloro-6-fluoro-4-trifluoromethylphenoxy)benzoyl]-N',N'-dimethyl hydrazide (1g), prepared as described in Example 1(b) was dissolved in dry toluene (10 cm$^3$) and a solution of dimethyl sulphate (0.31g) in dry toluene (3 cm$^3$) added. The reaction mixture was stirred under reflux for 4½ hours and then left to stand at room temperature overnight.

The solution was then concentrated to a solid residue which was washed twice with diethyl ether and air dried. The remaining solid (yield 1.09 g., mp 172–174° C.) was confirmed by nmr analysis to be compound 14 in Table 1.

EXAMPLE 15

This Example illustrates the preparation of compound No. 15 in Table 1.

N-[2-nitro-5-(2,6-difluoro-4-trifluoromethylphenoxy)benzoyl-N', N'-dimethyl hydrazide (1.22 g), prepared as described in Example 7(b), was fused with ethyl p-toluene sulphate (1.8 g) at approximately 140° C. for 2 hours and, after being left to stand overnight at room temperature, heated again to approximately 140° C. for a further 8 hours. A viscous oil was obtained. Trituration of the oil firstly with diethyl ether/petrol mixture and then with cyclohexane gave a sticky white brown solid which was isolated by decantation. This solid (1.04 g) was confirmed by nmr and mass spectroscopy to be compound 15 in Table I.

Biological Data

This data illustrates the herbicidal properties of compounds of Tables I and II. The compounds were submitted to herbicide tests as described below.

Each compound in the appropriate concentration was incorporated into a 4% emulsion of methyl cyclohexanone and a 0.4% blend of 3.6 parts Tween 20 and 1 part Span 80. Tween 20 is a Trade Mark for a surface active agent comprising a condensate of 20 molar proportions of ethylene oxide with sorbitan laurate. Span 80 is a Trade Mark for a surface-active agent comprising sorbitan monolaurate. Formulation was effected by dissolving the compound in the requisite amount of solvent/surfactant blend. If necessary, glass beads were added, the total liquid volume adjusted to 5 ml with water and the mixture shaken to effect complete dissolution of the compound. The formulation so prepared, after removal of beads where necessary, was then diluted to final spray volume (45 ml) with water.

The spray compositions so prepared were sprayed on to young pot plants (post-emergence test) at a rate equivalent to 1000 liters per hectare. Damage to plants was assessed 13 days after spraying by comparison with untreated plants, on a scale of 0 to 5 where 0 is 0–10% damage, 1 is 11 to 25% damage, 2 is 26–5% damage, 3 is 51–80% damage, 4 is 81–95% damage and 5 is 96–100% damage.

In a test carried out to detect pre-emergence herbicidal activity, seeds of the test species were placed on the surface of plastic trays of compost and sprayed with the compositions at the rate of 1000 liters per hectare. The seeds were then covered with further compost. 20 days after spraying, the seedlings in the sprayed plastic trays were compared with the seedlings in unsprayed control trays, the damage being assessed on the same scale of 0 to 5.

The results of the tests are given in Table III below.

TABLE III

| COMPOUND NO. | RATE OF APPLICATION kg/ha | PRE- OR POST-EMERGENCE APPLICATION | TEST PLANTS (see Table IV) | | | | | | |
|---|---|---|---|---|---|---|---|---|---|
| | | | Sb | Rp | Ct | Sy | Mz | Ww | Rc |
| 1 | 0.1 | Pre | 5 | 5 | 2 | 3 | 4 | 3 | 2 |
| 2 | 0.2 | Pre | 4 | 3 | 3 | 2 | 2 | 1 | 0 |
| | | Post | 1 | 1 | 5 | 4 | 3 | 2 | 2 |
| 3 | 0.1 | Pre | 5 | 5 | 4 | 3 | 4 | 4 | 4 |
| 4 | 1.0 | Pre | 5 | 5 | 3 | 3 | 5 | 4 | 5 |
| | | Post | 3 | 5 | 4 | 3 | 3 | 2 | 2 |
| 5 | 0.1 | Pre | 5 | 5 | 5 | 4 | 5 | 5 | 5 |
| | | Post | 5 | 5 | 4 | 5 | 5 | 5 | 5 |
| 6 | 0.1 | Pre | 5 | 5 | 5 | 2 | 5 | 5 | 5 |
| | | Post | 5 | 5 | 5 | 5 | 5 | 5 | 1 |
| 7 | 0.1 | Pre | 5 | 5 | 5 | 0 | 5 | 5 | 5 |
| | | Post | 5 | 5 | 5 | 2 | 3 | 2 | 1 |
| 8 | 0.1 | Pre | 5 | 5 | 4 | 4 | 5 | 4 | 5 |
| | | Post | 4 | 4 | 5 | 4 | 5 | 2 | 3 |
| 9 | 0.1 | Pre | 5 | 5 | 4 | 3 | 5 | 1 | 5 |
| | | Post | 3 | 3 | 5 | 3 | 1 | 1 | 1 |
| 10 | 0.2 | Pre | 5 | 5 | 4 | 2 | 5 | 3 | 3 |
| | | Post | 4 | 4 | 4 | 2 | 1 | 2 | 1 |
| 11 | 0.2 | Pre | 5 | 4 | 3 | 2 | 5 | 2 | 2 |
| | | Post | 2 | 3 | 4 | 3 | 2 | 2 | 1 |
| 12 | 0.2 | Pre | 0 | 3 | 1 | 3 | 3 | 1 | 0 |
| | | Post | 3 | 3 | 5 | 3 | 2 | 2 | 3 |
| 13 | 0.2 | Pre | 2 | 5 | 0 | 1 | 5 | 3 | 1 |
| | | Post | 2 | 2 | 4 | 2 | 3 | 2 | 1 |
| 14 | 0.1 | Pre | 4 | 4 | 1 | 4 | 5 | 3 | 5 |
| | | Post | 5 | 5 | 5 | 4 | 5 | 1 | 0 |
| 15 | 0.1 | Pre | 5 | 5 | 0 | 0 | 3 | 0 | 0 |
| | | Post | 4 | 4 | 5 | 4 | 4 | 2 | 2 |

| COMPOUND NO. | TEST PLANTS (see Table IV) | | | | | | | | | | | | | | | | |
|---|---|---|---|---|---|---|---|---|---|---|---|---|---|---|---|---|---|
| | Sn | Ip | Am | Pi | Ca | Ga | Xa | Ab | Co | Av | Dg | Al | St | Ec | Sh | Ag | Cn |
| 1 | 5 | 3 | 5 | 5 | 5 | 2 | 4 | 5 | 5 | 4 | 5 | 4 | 5 | 5 | 5 | 5 | 0 |
| 2 | 5 | 3 | 5 | 5 | 5 | — | 3 | 3 | 1 | 1 | 1 | 3 | 3 | 0 | 3 | 2 | 0 |
| | 5 | 3 | 5 | 2 | 5 | 3 | 2 | 3 | 2 | 1 | 1 | 1 | 2 | 2 | 3 | 1 | 1 |
| 3 | 5 | 5 | 5 | 5 | 5 | 5 | 5 | 5 | 5 | 5 | 5 | 5 | 5 | 5 | 4 | 4 | 1 |
| 4 | 5 | 3 | 5 | 2 | 5 | — | 3 | 5 | 1 | 3 | 4 | 3 | 4 | 5 | 5 | 5 | 1 |
| | 5 | 5 | 5 | 5 | 5 | 4 | 5 | 5 | 1 | 2 | 2 | 1 | 4 | 0 | 3 | 2 | 1 |
| 5 | 5 | 5 | 5 | 5 | 5 | — | 5 | 5 | 5 | 5 | 5 | 5 | 5 | 5 | 5 | 5 | 4 |
| | 5 | 5 | 5 | 5 | 5 | 5 | 5 | 5 | 4 | 5 | 5 | 5 | 5 | 5 | 5 | 5 | 4 |
| 6 | 5 | 5 | 5 | 3 | 5 | 0 | 5 | 5 | 5 | 5 | 5 | 5 | 5 | 5 | 5 | 5 | 0 |
| | 5 | 5 | 5 | 5 | 5 | 5 | 5 | 5 | 4 | 5 | 5 | 5 | 5 | 4 | 5 | 3 | 3 |
| 7 | 5 | 5 | 5 | 3 | 5 | 0 | 5 | 5 | 5 | 4 | 4 | 4 | 5 | 5 | 5 | 4 | 0 |
| | 5 | 5 | 5 | 5 | 5 | 4 | 5 | 5 | 2 | 1 | 2 | 2 | 3 | 3 | 1 | 1 | 2 |
| 8 | 5 | 4 | 4 | 4 | 5 | — | 4 | 5 | 5 | 4 | 4 | 4 | 5 | 5 | 5 | 5 | 2 |
| | 5 | 4 | 5 | 5 | 5 | 5 | 4 | 5 | 2 | 3 | 3 | 2 | 3 | 3 | 4 | 4 | 1 |
| 9 | 5 | 4 | 5 | — | 5 | — | 3 | 5 | 5 | 3 | 5 | 2 | 5 | 5 | 5 | 2 | 0 |
| | 5 | 5 | 5 | 5 | 5 | 3 | 3 | 5 | 2 | 1 | 2 | 2 | 4 | 3 | 2 | 1 | 0 |
| 10 | 5 | 3 | 5 | 3 | 5 | — | 4 | 5 | 4 | 3 | 3 | 3 | 5 | 5 | 3 | 4 | 0 |
| | 5 | 5 | 5 | 5 | 5 | 5 | 4 | 4 | 1 | 1 | 2 | 1 | 4 | 1 | 2 | 2 | 1 |
| 11 | 5 | 2 | 5 | 5 | 5 | — | 3 | 5 | 1 | 1 | 3 | 3 | 3 | 1 | 4 | 0 | 1 |
| | 5 | 3 | 5 | 3 | 5 | 2 | 3 | 3 | 3 | 2 | 2 | 2 | 3 | 1 | 2 | 1 | 2 |
| 12 | 4 | 1 | 3 | 4 | 5 | — | 1 | 5 | 0 | 1 | 0 | 2 | 3 | 0 | 2 | 1 | 0 |
| | 5 | 3 | 5 | 3 | 5 | 3 | 2 | 3 | 2 | 2 | 2 | 1 | 3 | 2 | 3 | 2 | 2 |
| 13 | 5 | 3 | 5 | 3 | 5 | — | 5 | 5 | 3 | 3 | 3 | 3 | 4 | 5 | 4 | 5 | 0 |
| | 5 | 4 | 5 | 5 | 5 | 5 | 4 | 4 | 1 | 1 | 2 | 1 | 4 | 0 | 2 | 1 | 1 |
| 14 | 5 | 4 | 5 | 0 | 5 | 0 | 4 | 5 | 5 | 4 | 5 | 3 | 5 | 5 | 5 | 0 | 0 |
| | 5 | 5 | 5 | 5 | 5 | 3 | 5 | 5 | 4 | 2 | 3 | 2 | 5 | 5 | 3 | 0 | 1 |
| 15 | 5 | 0 | 5 | 3 | 5 | 4 | 2 | 3 | 3 | 0 | 2 | 0 | 0 | 4 | 0 | 5 | 0 |
| | 4 | 4 | 5 | 4 | 4 | 4 | 4 | 4 | 0 | 1 | 4 | 1 | 2 | 3 | 3 | 1 | 0 |

TABLE IV

| Abbreviations used for Test Plants | |
|---|---|
| Sb | Sugar Beet |
| Rp | Rape |
| Ct | Cotton |
| Sy | Soybean |
| Mz | Maize |
| Ww | Winter wheat |
| Rc | Rice |
| Sn | *Senecio vulgaris* |
| Ip | *Ipomoea purpurea* |

TABLE IV-continued

| Abbreviations used for Test Plants | |
|---|---|
| Am | *Amaranthus retroflexus* |
| Pi | *Polygonum aviculare* |
| Ca | *Chenopodium album* |
| Ga | *Galium aparine* |
| Xa | *Xanthium spinosum* |
| Ab | *Abutilon theophrasti* |
| Co | *Cassia obtusifolia* |
| Av | *Avena fatua* |
| Dg | *Digitaria sanguinalis* |
| Al | *Alopercurus myosuroides* |
| St | *Setaria viridis* |
| Ec | *Echinchloa crus-galli* |
| Sh | *Sorghum halepense* |
| Ag | *Agropyron repens* |
| Cn | *Cyperus rotundus* |

CPH/CF
PP 33688
03 Nov 86

What is claimed is:

1. A compound of formula (I)

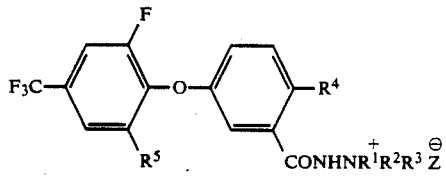

or a zwitterion derivative thereof; wherein
$R^1$, $R^2$ and $R^3$ are each independently optionally substituted alkyl or $R^1$ and $R^2$ together with the nitrogen atom to which they are attached form a 5- or 6-membered heterocyclic ring;
$R^4$ is hydrogen, nitro, halo, alkyl or $CF_3$;
$R^5$ is halo; and
Z is an anion.

2. A compound according to claim 1 wherein $R^1$, $R^2$ and $R^3$ are selected from $C_{1-4}$ alkyl optionally substituted by aryl, halo, nitrile, haloalkyl, $CO_2R^6$, $OR^6$ or $S(O)_n$ $R^6$ wherein $R^6$ is hydrogen or a hydrocarbyl group and n is 0, 1 or 2.

3. A compound according to claim 1 or claim 2 wherein $R^1$, $R^2$ and $R^3$ are selected from methyl, ethyl or benzyl.

4. A compound according to claim 1 wherein $R^5$ is chloro or fluoro.

5. A compound according to claim 1 wherein $R^4$ is nitro, chloro or trifluoromethyl.

6. A compound selected from salts and Zwitterions of compounds of formula (I) as defined in claim 1 wherein:
N-[(5-(2-chloro-α,α,α,6-tetrafluoro-p-tolyloxy)-2-nitro)benzamido]-N-methylpiperidinium;
2-chloro-5-(2-chloro-α,α,α,6-tetrafluoro-p-tolyloxy)-N,N,N-trimethylbenzoylhydrazinium;
N,N-dimethyl-N-ethyl-2-nitro-5(α,α,α,2,6-pentafluoro-p-tolyloxy)benzoylhydrazinium tosylate;
N-ethyl-N,N-dimethyl-2-nitro-5-(α,α,α,2,6-pentafluoro-p-tolyloxy)benzoylhydrazinium tosylate;
2-chloro-5-(2-chloro-α,α,α,6-tetrafluoro-p-tolyloxy)N-ethyl-N,N-dimethylbenzoylhydrazinium;
N-benzyl-2-chloro-5-(2-chloro-α,α,α,6-tetrafluoro-p-tolyloxy)-N,N-dimethylbenzoylhydrazinium;
5-(2-chloro-α,α,α,6-tetrafluoro-p-tolyloxy)-N-ethyl-N,N-dimethyl-2-nitrobenzoylhydrazinium;
N-benzyl-5-(2-chloro-α,α, α,6-tetrafluoro-p-tolyloxy)-N,N-dimethyl-2-nitrobenzoylhydrazinium;
5-(2-chloro-α,α,α,6-tetrafluoro-p-tolyloxy)-N,N,N-trimethyl-2-nitrobenzoylhydrazinium;
N,N,N-trimethyl-2-nitro-5-(α,α,α,2,6-pentafluoro-p-tolyloxy)benzoylhydrazinium;
2-chloro-5-(2-chloro-α,α, α,6-tetrafluoro-p-tolyloxy)-N,N,N-trimethylbenzoylhydrazinium;
2-chloro-N,N,N-trimethyl-5-(α,α,α,2,6-pentafluoro-p-tolyloxy)benzoylhydrazinium;
N-[(5-(2-chloro-α,α,α,6-tetrafluoro-p-tolyloxy)-2-nitrobenzamido]-N-methylmorpholinium;
N-[2-chloro-5-(2-chloro-α,α,α,6-tetrafluoro-p-tolyloxy)benzamido]-N-methylmorpholinium; and
N-[2-chloro-5-(2-chloro-α,α,α,6-tetrafluoro-p-tolyloxy)benzamido]-N-methylpiperidinium.

7. A herbicidal composition comprising a compound of formula (I) as defined in claim 1 in combination with a solid or liquid diluent.

8. A process for inhibiting the growth of unwanted plants which process comprises applying to the plants or to a locus thereof a compound of formula (I) as defined in claim 1.

* * * * *